(12) United States Patent
Kobayashi et al.

(10) Patent No.: US 8,858,527 B2
(45) Date of Patent: Oct. 14, 2014

(54) CATHETER HAVING DENATURED PART FOR CONTACT WITH BODY

(75) Inventors: Tomohiro Kobayashi, Wako (JP); Yoshiaki Suzuki, Wako (JP); Tomonori Miyazato, Wako (JP); Hiroshi Ujiie, Wako (JP)

(73) Assignee: Riken, Saitama (JP)

( * ) Notice: Subject to any disclaimer, the term of this patent is extended or adjusted under 35 U.S.C. 154(b) by 1811 days.

(21) Appl. No.: 11/885,032

(22) PCT Filed: Feb. 23, 2006

(86) PCT No.: PCT/JP2006/303263
§ 371 (c)(1),
(2), (4) Date: Jul. 2, 2008

(87) PCT Pub. No.: WO2006/090776
PCT Pub. Date: Aug. 31, 2006

(65) Prior Publication Data
US 2009/0024109 A1    Jan. 22, 2009

(30) Foreign Application Priority Data

Feb. 24, 2005  (JP) ................. 2005-048199

(51) Int. Cl.
*A61M 25/00* (2006.01)
*A61M 5/32* (2006.01)
*A61L 29/14* (2006.01)
*A61L 29/06* (2006.01)

(52) U.S. Cl.
CPC .......... *A61M 25/0045* (2013.01); *A61L 29/14* (2013.01); *A61L 29/06* (2013.01); *A61L 2400/18* (2013.01)
USPC ........... 604/523; 604/264; 604/265; 604/266

(58) Field of Classification Search
USPC .............. 604/264–266, 272, 523–525, 890.1; 204/192.1–192.37; 315/111.21–111.91
See application file for complete search history.

(56) References Cited

U.S. PATENT DOCUMENTS 4,064,030 A    12/1977   Nakai et al.
4,927,676 A *  5/1990   Williams et al. ............... 424/423
(Continued)

FOREIGN PATENT DOCUMENTS

JP    51-125455 A    11/1976
JP     5-49689 A     3/1993
(Continued)

OTHER PUBLICATIONS

Chu, P.K. et al., "Plasma-surface modification of biomaterials", Materials Science and Engineering R: Reports, Elsevier Sequoia S.A., Lausanne, CH, vol. 36, No. 5-6, Mar. 29, 2002, pp. 143-206, XP004343705.

(Continued)

*Primary Examiner* — Emily Schmidt
*Assistant Examiner* — Lauren M Peng
(74) *Attorney, Agent, or Firm* — Birch, Stewart, Kolasch & Birch, LLP

(57) ABSTRACT

It is an object of the present invention to provide a catheter, whereby a tunnel infection route is closed such that infection can be prevented, by improving adhesiveness between a medical catheter and a biologically-derived adhesive (fibrin adhesive), cells, or biological tissue. The present invention provides a medical catheter which is composed of material selected from the group consisting of silicone, polyurethane, polypropylene and polytetrafluoroethylene (PTFE), at least a portion of the surface of which is modified by plasma ion implantation.

8 Claims, 10 Drawing Sheets

(56) References Cited

U.S. PATENT DOCUMENTS

| | | | |
|---|---|---|---|
| 5,308,704 | A | 5/1994 | Suzuki et al. |
| 5,906,824 | A * | 5/1999 | Suzuki et al. ............... 424/402 |
| 6,403,167 | B1 | 6/2002 | Lee et al. |
| 6,504,307 | B1 | 1/2003 | Malik et al. |
| 7,201,935 | B1 * | 4/2007 | Claude et al. ............... 427/2.1 |
| 2001/0002000 | A1 * | 5/2001 | Kumar et al. ............. 204/192.1 |

FOREIGN PATENT DOCUMENTS

| | | |
|---|---|---|
| JP | 5-57011 A | 3/1993 |
| JP | 06-168930 A | 6/1994 |
| JP | 6-285151 A | 10/1994 |
| JP | 10-28728 A | 2/1998 |
| JP | 63-46165 A | 2/1998 |
| JP | 10-108909 A | 4/1998 |
| JP | 2000-54125 A | 2/2000 |
| JP | 2002-88179 A | 3/2002 |
| JP | 2002-509010 A | 3/2002 |
| JP | 2002-315821 A | 10/2002 |
| JP | 2003-171767 A | 6/2003 |
| JP | 2004-89361 A | 3/2004 |
| WO | WO-99/36276 A1 | 7/1999 |
| WO | WO-00/45892 A1 | 8/2000 |

OTHER PUBLICATIONS

Huang, N. et al., "Surface Modification of Blood Contacting Biomedical Implants by Plasma Processes", AIP Conference Proceedings, vol. 669, 2003, pp. 330-334; XP002611166.

Lee, J-S. et al., "Selective adhesion and proliferation of cells on ion-implanted polymer domains", Biomaterials, Elsevier Science Publishers BV., Barking, GB, vol. 14, No. 12, Oct. 1, 1993, pp. 958-960, XP024141830.

European Search Report of EP 06714403.0 (from PCT/JP2006/303263)—Dec. 6, 2010.

Rad, A. Yousefi, et al., "Adhesion of Different Bacterial Strains to Low-temperature Plasma Treated Biomedical Silicon Catheter Surfaces," J. Bioactive Compatible Polymers, vol. 13, No. 2, pp. 81-101 (1998).

Office Action dated May 24, 2011 issued in corresponding Japanese Patent Application No. 2005-048199.

Office Action dated Nov. 8, 2011 issued in corresponding Japanese Patent Application No. 2005-048199.

* cited by examiner (a) Upon RF pulse application  (b) Upon high-voltage negative pulse application

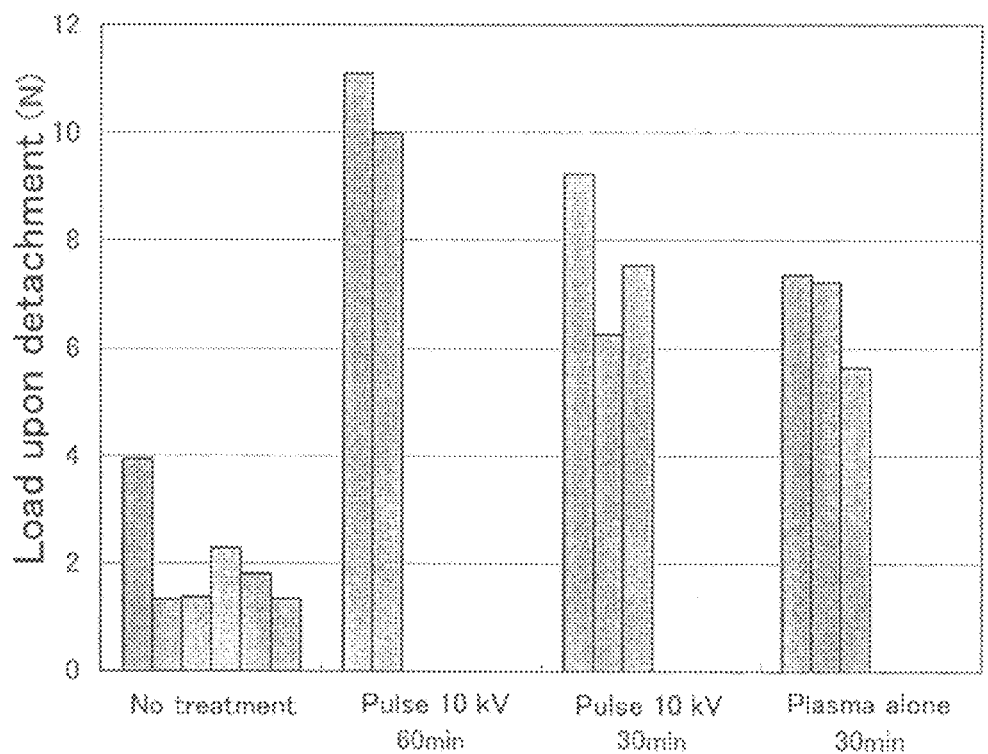

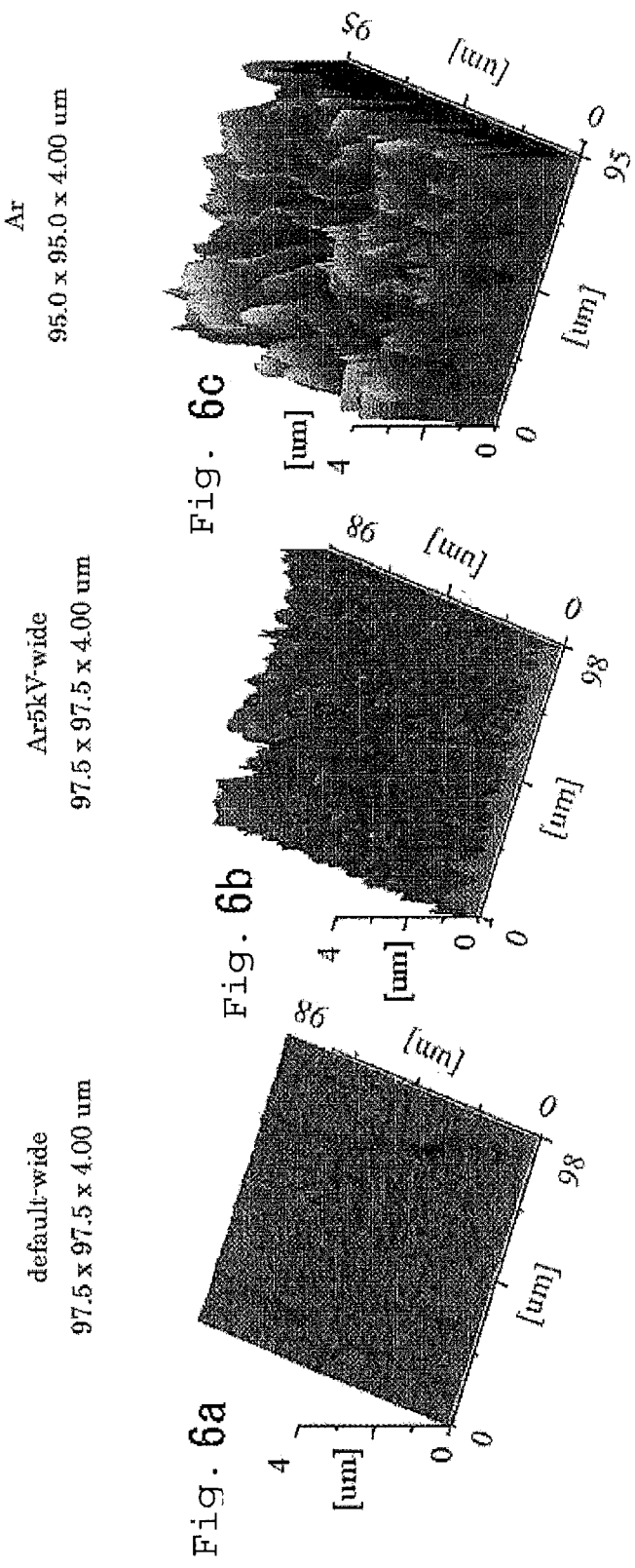

CATHETER HAVING DENATURED PART FOR CONTACT WITH BODY

BACKGROUND OF THE INVENTION

1. Technical Field

The present invention relates to a catheter having denatured part for contact with body and the method of producing the same.

2. Background Art

The occurrence of infectious diseases caused by catheter placement can be prevented by improving compatibility between catheters and biological tissue. A variety of attempts have been made to cover a biocompatible product with a membrane that is excellent in biocompatibility. In particular, many methods of covering using a hydroxyapatite membrane have been suggested. Examples of a method of forming a hydroxyapatite membrane include a plasma spraying method (e.g., JP Patent Publication (Kokai) No. 63-46165 A (1988)), a sputtering deposition method (e.g., JP Patent Publication (Kokai) No. 63-46165 A (1988)), a method comprising modifying a calcium phosphate compound membrane into a hydroxyapatite membrane by hydrothermal reaction (JP Patent Publication (Kokai) No. 5-57011 A (1993)), and a method for film deposition of hydroxyapatite contained in a supersaturated calcium phosphate compound solution on a product to be subjected to film deposition (JP Patent Publication (Kokai) No. 6-285151 A (1994)). In addition, a biocompatible catheter having a membrane comprising highly biocompatible ceramic (JP Patent Publication (Kokai) No. 10-28728 A (1998)) and the like have been disclosed. However, these attempts have not been analyzed in detail in terms of bioreactivity and have not been examined with animal experiments. Thus, none of them have been applied in practice.

Meanwhile, JP Patent Publication (Kokai) No. 5-49689 A (1993) discloses a cell adhesive material, which is composed of polymeric material comprising carbon as a constitutional element, and at least a portion of the surface of which is modified by ion bombardment. Further, JP Patent Publication (Kokai) No. 2002-315821 A discloses a material that adheres to bone and/or fascia, which is composed of polymeric material comprising carbon as a constitutional element and at least a portion of the surface of which is modified by ion bombardment. Furthermore, JP Patent Publication (Kokai) No. 2004-89361 A discloses a biological repair material compatible with a biological tissue adhesive (a polymeric material used in combination with a biological tissue adhesive, which comprises carbon or silicon as a constitutional element and at least a portion of the surface of which is modified by ion bombardment).

DETAILED DESCRIPTION OF THE INVENTION

Object of the Invention

It is an object of the present invention to provide a catheter, whereby a tunnel infection route is closed such that infection can be prevented, by improving adhesiveness between a medical catheter, such as a continuous ambulatory (mobile) peritoneal dialysis (CAPD) catheter, a central venous catheter, a hemodialysis shunt catheter or a ventricular drainage catheter and a biologically-derived adhesive (fibrin adhesive), cells, or biological tissue.

Means for Solving the Object

As a result of intensive studies to achieve the above object, the present inventors have found that infection can be prevented with closure of a tunnel infection route by modifying an interface part for contact with body on the outer side of a medical catheter by a plasma ion irradiation method so as to improve adhesiveness between the medical catheter and a biologically-derived adhesive (fibrin adhesive), cells, or biological tissue. This has led to the completion of the present invention.

Thus, the present invention provides a medical catheter which is composed of material selected from the group consisting of silicone, polyurethane, polypropylene and polytetrafluoroethylene (PTFE), at least a portion of the surface of which is modified by plasma ion implantation.

Another aspect of the present invention provides a method of producing a medical catheter, which comprises modifying at least a portion of the surface of a material selected from the group consisting of silicone, polyurethane, polypropylene and polytetrafluoroethylene (PTFE) by plasma ion implantation.

Preferably, the medical catheter of the present invention is composed of silicone.

Preferably, a high-voltage negative pulse is applied to plasma-exposed material selected from the group consisting of silicone, polyurethane, polypropylene and polytetrafluoroethylene (PTFE) so as to attract ions such that the surface of the material is omnidirectionally irradiated with the ions.

Preferably, plasma ions are selected from the group consisting of $He^+$, $Ne^+$, $Ar^+$, and $Kr^+$.

Preferably, the plasma ion pressure during treatment is $1.0\times10^{-1}$ to $1.0\times10^{-4}$ torr, and the treatment time of plasma ion implantation is 1 minute to 3 hours.

BEST MODE FOR CARRYING OUT THE INVENTION

Hereafter, embodiments of the present invention are described in detail.

The present invention relates to a medical catheter which is composed of material selected from the group consisting of silicone, polyurethane, polypropylene and polytetrafluoroethylene (PTFE), at least a portion of the surface of which is modified by plasma ion implantation.

The material of the catheter of the present invention can be selected from the group consisting of silicone, polyurethane, polypropylene, and polytetrafluoroethylene (PTFE). Preferably, such material is silicone. Silicone is polymeric material having a structure in which basic units of Si—O are polymerized. The type of silicone used in the present invention is not particularly limited as long as it can be used for catheters.

In the case of the catheter of the present invention, at least a portion of the surface of the above material is modified by plasma ion implantation.

The plasma ion implantation method used in the present invention is a method wherein a high-voltage negative pulse is applied to a plasma-exposed sample to be subjected to irradiation so as to attract ions such that the surface of a sample is omnidirectionally irradiated with the ions. Examples of a plasma generation method include a plasma generation method using a parallel plate electrode, a loop antenna, or the like and a method comprising directly applying a high frequency wave to a sample. The plasma ion implantation method is advantageous in that, unlike ion beam irradiation techniques using conventional linear accelerators, even a sample to be subjected to irradiation having a curved surface can be uniformly irradiated with ions. In addition, such sample may be a conductor or an insulator. According to the present invention, it has been revealed that a polymer catheter can be uniformly modified in a short period of time by applying the plasma ion implantation method to treat the surface of the polymer catheter which is the curved surface of an insulator. In particular, in cases in which a sample is a catheter (in a tubular shape), a piece of wire having a diameter almost equivalent to the inner diameter of the sample may be introduced inside the sample, and in such cases the sample is then allowed to stand on a sample holder, followed by plasma ion implantation treatment. According to the present invention, cell adhesiveness of the catheter material and adhesiveness of a biological adhesive can be significantly improved through modification by plasma ion implantation.

Examples of ion species to be implanted include, but are not particularly limited to, $H^+$, $He^+$, $C^+$, $N^+$, $Ne^+$, $Na^+$, $N_2^+$, $O^+$, $Ar^+$, and $Kr^+$. Of these, $He^+$, $Ne^+$, $Ar^+$, and $Kr^+$ are particularly preferable.

For instance, the rate for introducing a gas comprising any of the above examples may be 5 to 50 ml/min. The pressure during treatment may be $1.0 \times 10^{-1}$ to $1.0 \times 10^{-4}$ torr. The voltage applied to a sample may be 0 to −50.0 kV, for example, and preferably 0 to −20.0 kV. In addition, the treatment time of plasma ion implantation is not particularly limited as long as effects of the present invention can be achieved. However, such treatment time may be generally 1 minute to 3 hours and preferably 5 minutes to 1 hour. In the case of a treatment time of less than 1 minute, effects of the present invention cannot be achieved, which is not preferable. Meanwhile, in the case of a treatment time of more than 3 hours, the structure of catheter material tends to be destroyed, which is not preferable.

As described above, cell adhesiveness and the adhesive property of a biologically derived adhesive (fibrin adhesive) can be significantly improved by allowing a catheter material such as silicone to be subjected to plasma ion irradiation. Such improvement in cell adhesiveness is considered to be caused by surface carbonization and an increase in the amount of adhering proteins as a result of introduction of functional groups. Further, such improvement in the adhesive property of a fibrin adhesive is considered to be caused by surface carbonization and an increase in surface area. The catheter of the present invention is effective for prevention of tunnel infection. This is because a fibrin adhesive tightly adheres to a catheter at the beginning of catheter introduction, while on the other hand, biological tissue tightly adheres to the catheter after decomposition and absorption of the fibrin adhesive.

The present invention is hereafter described in greater detail with reference to the following examples, although the technical scope of the present invention is not limited thereto.

EXAMPLES (1) Overview

Samples of silicone used in medical practice were subjected to plasma ion irradiation such that a part for contact with living body was modified. Modification effects were evaluated by tensile strength tests using a biologically-derived adhesive and ex vivo cell adhesion tests. Surfaces of the modified samples were subjected to measurements of morphology, compositions, binding states, and the like by AFM, RAMAN, or RBS. The measurement results were examined in connection with the aforementioned property-improving effects.

(2) Sample Preparation

The silicone material used was THE740 (obtained by mixing polyorganosiloxane and silicon dioxide followed by pressing) produced by GE Toshiba Silicones. The structure thereof contains two Si—O chains bound to each other as shown below.

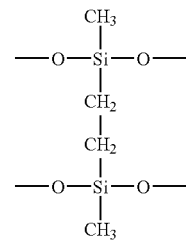

Samples were produced by the plasma ion irradiation method. According to the plasma ion irradiation method, a high-voltage negative pulse is applied to a plasma-exposed sample so as to attract ions such that the sample surface is irradiated with the ions. In the plasma generation method, a parallel plate electrode, a loop antenna, or the like may be used. Herein, a method comprising directly applying a high frequency wave to a sample was used. FIG. 1 shows a schematic view of an irradiation system. The method used herein is advantageous in that plasma generation takes place in a manner such that the whole sample is covered by plasma. FIG. 2 illustrates the principle of ion irradiation. First, a high frequency (RF) pulse is applied to a sample such that gas around the sample is ionized, resulting in plasma generation (FIG. 2(a)). Before plasma disappearance, a high-voltage negative pulse is applied to the sample so as to attract positively charged ions, followed by ion irradiation (FIG. 2(b)). According to the above method, ion irradiation can be carried out regardless of whether or not a sample to be subjected to irradiation is conductive. In cases in which a sample is in a sheet form, the sample is attached to a sample holder by using a conductive double-sided adhesive tape, followed by treatment. In cases in which a sample is in a catheter form (tubular shape), a piece of wire having a diameter almost equivalent to the inner diameter of the sample is introduced inside the sample and the sample is then allowed to stand on a sample holder, followed by treatment.

The ion species (introduced gas) used was He, Ar, or Kr. The rate of gas introduction was designated as 20 cc/min. The pressure during treatment was designated as $1.0 \times 10^{-2}$ torr. The applied voltage was designated as 0, −2.5, −5.0, −7.5, or −10.0 kV. The treatment time was designated as 30 minutes in all cases except for the case shown in FIG. 5 (60 minutes).

In addition, the high frequency pulse width and the high-voltage negative pulse width were designated as 30 μsec and 10 μsec, respectively. In addition, the interval between the ending point of the RF pulse and the starting point of the high-voltage negative pulse was designated as 25 μsec. The RF output was 500 W, and the pulse repetition rate was 2 kHz. FIG. 3 shows examples of a current and a voltage measured using an oscilloscope during irradiation.

(3) Results (1) Improvement in the Adhesive Property of a Fibrin Adhesive

A silicone sheet that had been irradiated with ions was cut into rectangles 5 mm×15 mm in size. The rectangles were adhered to cardboard pieces having the same size with the use of a fibrin adhesive. At such time, each adhesion surface was determined to have a size of 5 mm×5 mm (FIG. 4). After 2 hours of drying at ordinary temperature, the load upon detachment was measured when tension was applied to each rectangle in the horizontal direction at a rate of 5 mm per minute. Because of strong adhesion between the cardboard pieces and the fibrin adhesive, detachment always occurred at an interface between silicone and the adhesive. Measurement was carried out using a horizontal digital load gauge (Model 2255, Aikoh Engineering Co., Ltd.). FIG. 5 shows results of load measurement upon detachment of untreated samples, treated samples (10 kV-Ar-1 hour), other treated samples (10 kV-Ar-30 min), and samples subjected to Ar plasma exposure alone. Due to plasma exposure, the adhesive property of the fibrin adhesive was found to increase by approximately 1.5 times compared with the cases of untreated samples. As a result of application of ion irradiation, such adhesive property was found to increase by approximately 2.5 times at most compared with the cases of untreated samples. Also, upon energy irradiation at less than 10 kV, similar improvement in adhesive property was observed.

(2) Changes in Surface Morphology

FIG. 6 shows AFM images of untreated samples (a), treated samples (Ar-5 kV-30 min) (b), and other treated samples (Ar-10 kV-30 min) (c). The surface roughness increased along with the increase in treatment voltage. It is considered that the increase in surface area (adhesion surface area) caused improvement in the adhesive property of the fibrin adhesive. In addition, it is considered that strength against tension, particularly in the horizontal direction, increased due to the invasion of fibrin adhesive into concave portions.

(3) Changes in Cell Adhesiveness

FIG. 7 shows optical microscopic images of an unirradiated sample (a) and a treated sample (Ar-7.5 kV-30 min) (b) on day 3 of culture after seeding of mouse-derived fibroblasts. The numbers of cells are obviously different. However, the focus herein is the ratio of cells adhering to the sample surface (elongated shape) to cells not adhering thereto (round shape). In FIG. 8, the horizontal axis represents negative pulse voltage, and the vertical axis represents cell adhesion rate. (In each case, the gas introduced was Ar and the treatment time was 30 minutes). Compared with the untreated sample, a significant improvement in cell adhesiveness was observed in the sample treated with a negative pulse voltage of 0 to 7.5 kV. Meanwhile, cell adhesiveness of the sample treated with a negative pulse voltage of 10 kV was almost equivalent to that of the sample that had not been irradiated.

(4) Changes in Surface Composition

FIG. 9 shows RBS spectra of silicone samples subjected to Ar plasma ion irradiation. In each case, the treatment time was 30 minutes. Argon ions used for irradiation and iron ions that were thought to be released from the inner wall of a vacuum chamber were confirmed to exist on each sample surface except in the cases of an untreated sample and a sample treated with a pulse voltage of 0 kV. These elements were found in minute amounts. Further, only small portions thereof were exposed on the sample surface. Consequently, it is considered that the existence of such elements does not substantially influence the adhesive property of a fibrin adhesive or cell adhesiveness. Along with the increase in pulse voltage, decreases in Si and O on the sample surface were observed. Thus, the percentage of C relative to Si and O increased, resulting in changes in not only the surface shape but also the adhesive property of a fibrin adhesive and cell adhesiveness.

FIG. 10 shows Raman spectra, based on which it is understood the decrease in methyl groups (approximately 2900 $cm^{-1}$) was caused by the increase in pulse voltage, indicating that the silicone structure was destroyed. Meanwhile, in the case of 10 kV irradiation, a graphite-derived peak (approximately 1560 $cm^{-1}$) and an amorphous carbon-derived peak (approximately 1350 $cm^{-1}$) were obviously observed. Accordingly, it is understood that surface carbonization is promoted by the increase in pulse voltage.

Summary of (1) to (4)

As a result, it has been shown that cell adhesiveness and the adhesive property of a biologically-derived adhesive (fibrin adhesive) can be significantly improved by plasma ion irradiation of silicone. The improvement in cell adhesiveness is thought to be caused by surface carbonization and the increase in the amount of adhering proteins due to introduction of functional groups. In addition, the improvement in the adhesive property of a fibrin adhesive is thought to be caused by surface carbonization and the increase in surface area. It is considered that, when the above method is applied to treat a catheter surface, tunnel infection can be effectively prevented because the fibrin adhesive tightly adheres to the catheter at the beginning of catheter introduction, while on the other hand, biological tissue tightly adheres to the catheter after decomposition and absorption of the fibrin adhesive.

(5) Regarding Fibrin Adhesive Adhesion Tests

FIG. 11 shows results of fibrin adhesive shearing strength measurement tests using three different ions. Significant increases in adhesive property were confirmed except for the case of the sample treated with helium at 0 kV (plasma exposure alone). In addition, the applied voltage was proportional to the shearing strength.

(6) Regarding Cell Adhesion Tests

FIG. 12 shows irradiation voltage dependences of cell adhesion rates and numbers of cells in connection with three different ions. The cell adhesion rate and the number of cells each temporarily increased and then decreased after reaching maximum value. In particular, the maximum point of the cell adhesion rate tended to move to the low voltage side along with the increase in the ion mass number. Therefore, it is understood that the modification rate becomes greater in the cases of heavier ions at an identical voltage.

(7) Regarding FT-IR Measurement Results

FIG. 13 shows FT-IR (Fourier-transform infrared) spectra of argon-irradiated samples. In FIG. 13, the positions "A" and "B" correspond to hydroxyl groups (—OH) and adsorption water, respectively. The higher the treatment voltage, the greater the amounts of such hydroxyl groups and adsorption water. Consequently, it is expected that the surface state was modified to become hydrophilic. In FIG. 13, the position "C" corresponds to carbonyl groups (C=O). At 5 kV and 7.5 kV, peaks appeared. However, no clear peak was observed at 10 kV. Such peak appearance corresponds to cell adhesiveness behavior. Thus, carbonyl groups may contribute to some extent to adsorption of proteins serving as scaffolds for surface cell adhesion.

INDUSTRIAL APPLICABILITY

According to the present invention, it has become possible to provide a catheter having cell adhesiveness and the adhesive property of a biologically derived adhesive (fibrin adhesive) and a method of producing the same.

BRIEF DESCRIPTION OF THE DRAWINGS

FIG. 5 shows results of tests regarding the adhesive property of a fibrin adhesive.

FIG. 6 shows results of observation of surface morphology by AFM.

Figure 1:
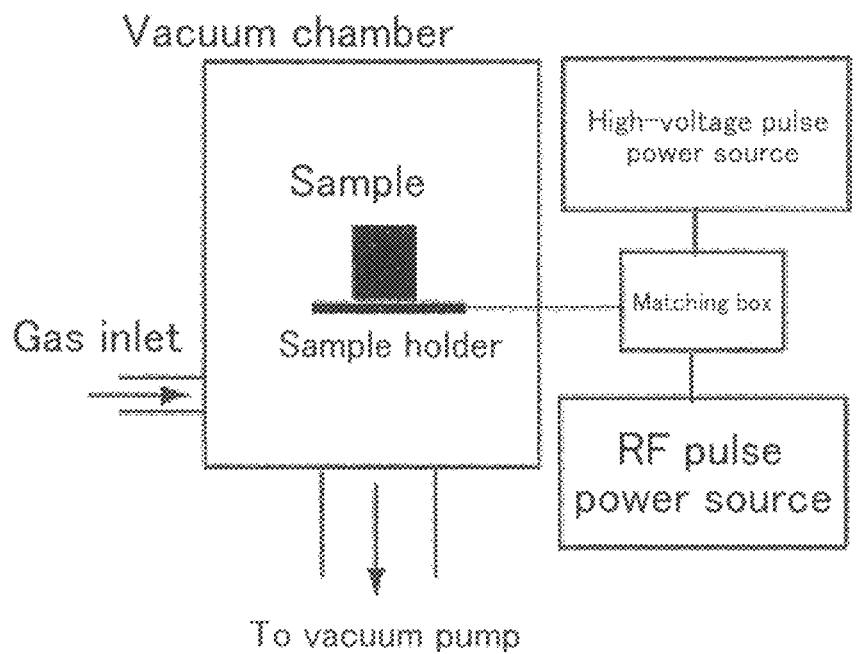
FIG. 1 shows an overview of a plasma ion irradiation apparatus.
Figure 2:
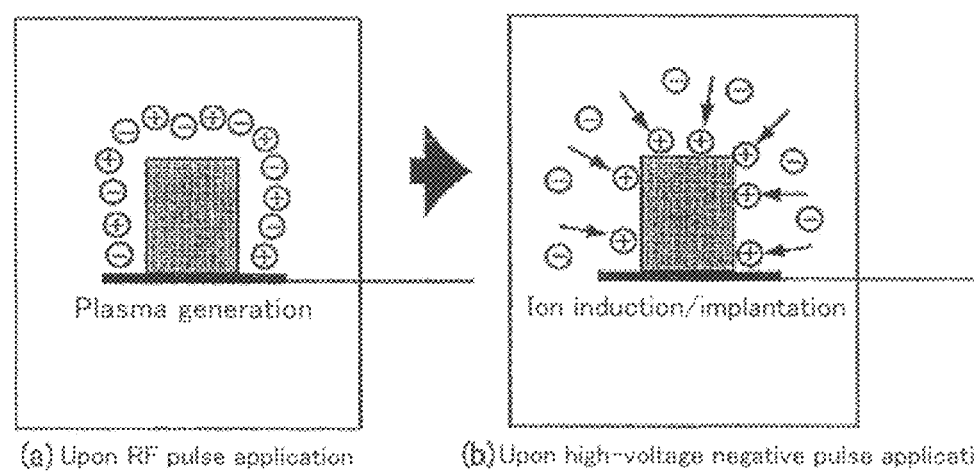
FIG. 2 illustrates the principle of ion irradiation.
Figure 3:
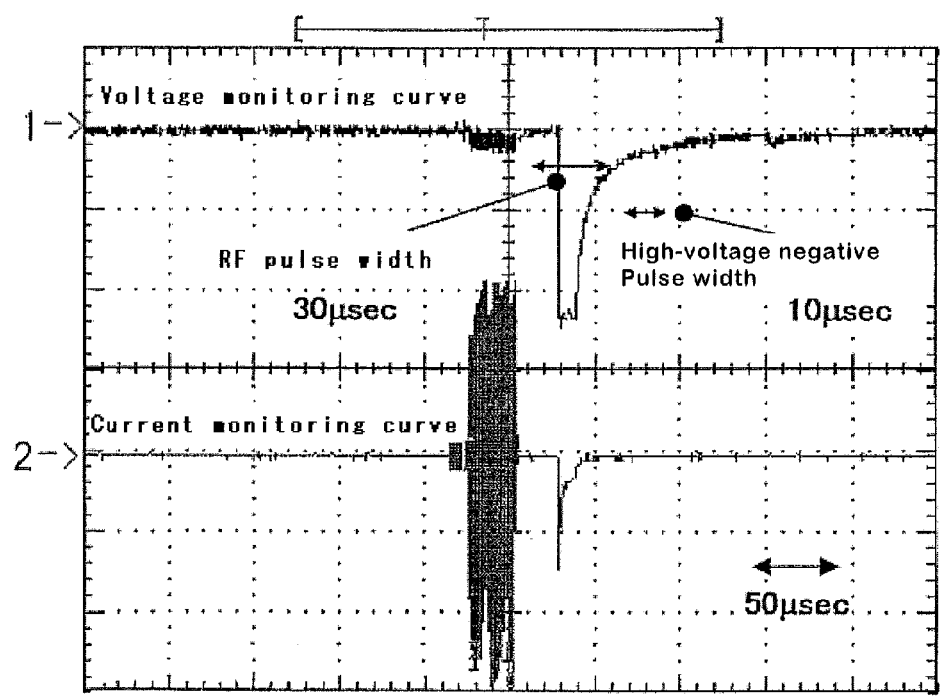
FIG. 3 shows an RF pulse and a high-voltage negative pulse.
Figure 4:
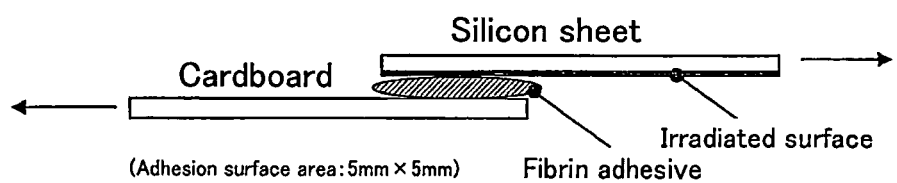
FIG. 4 illustrates a piece tested regarding the adhesive property of a fibrin adhesive (side view).
Figure 7A:
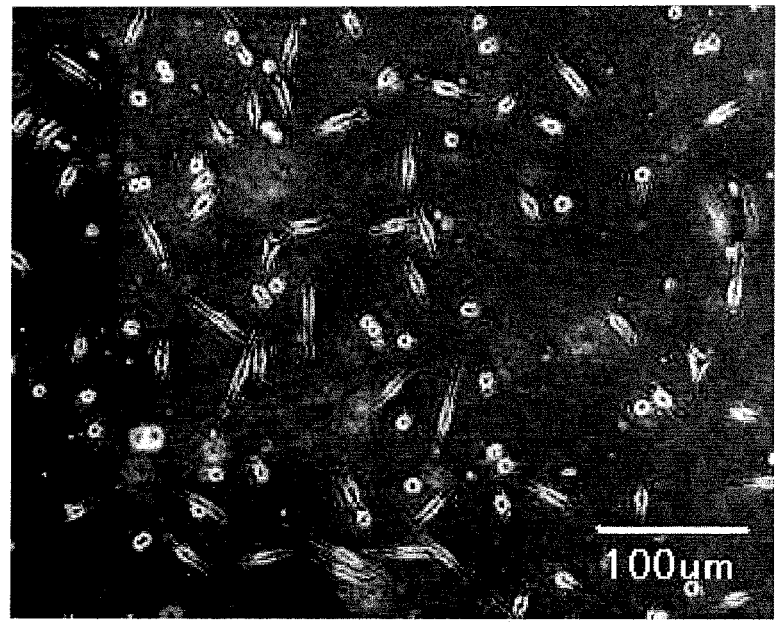
FIG. 7 shows results of observation of cell adhesion states.
Figure 7B:
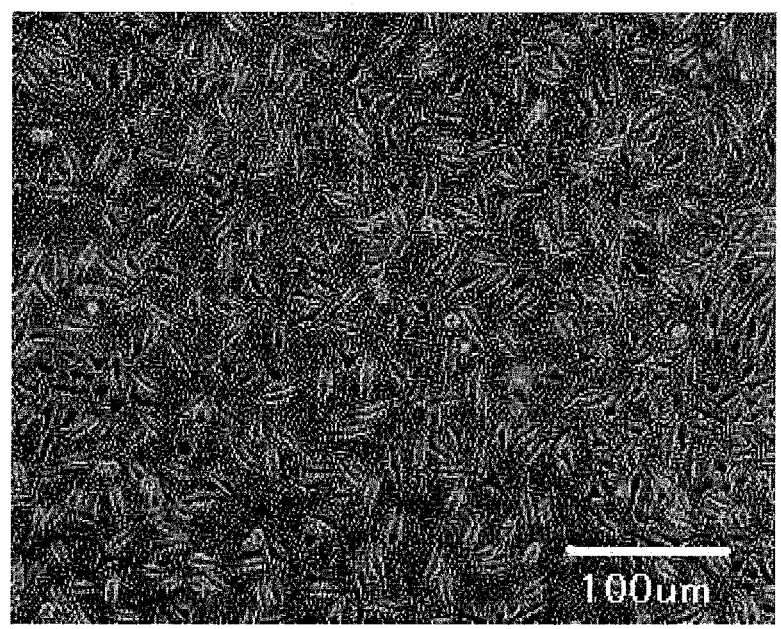
Figure 8:
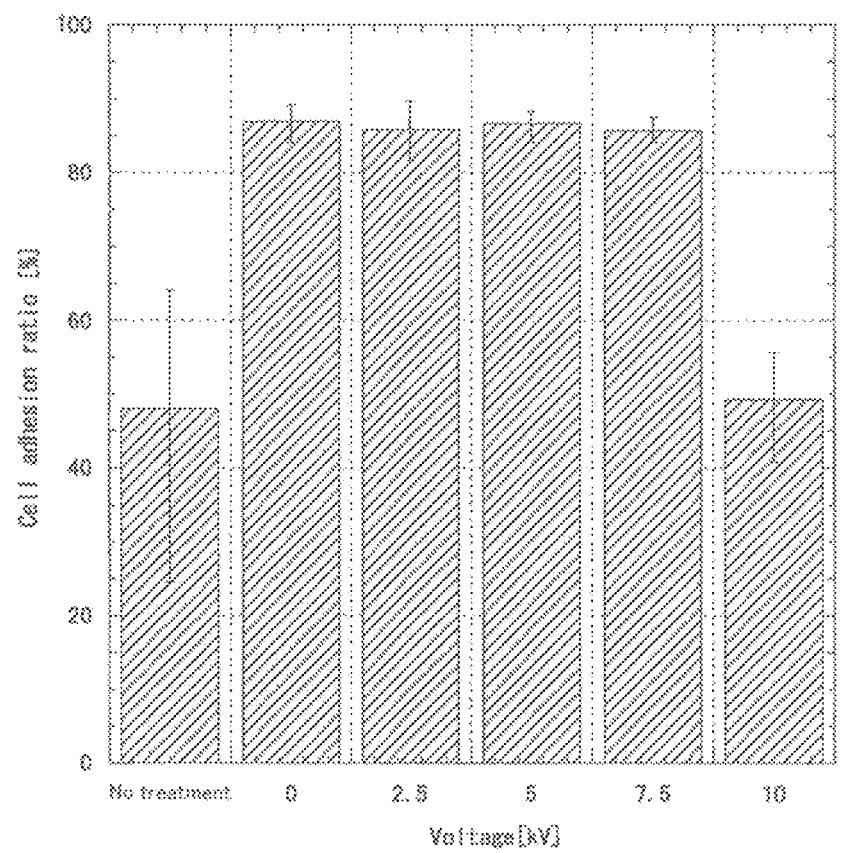
FIG. 8 shows changes in cell adhesion rates.
Figure 9:
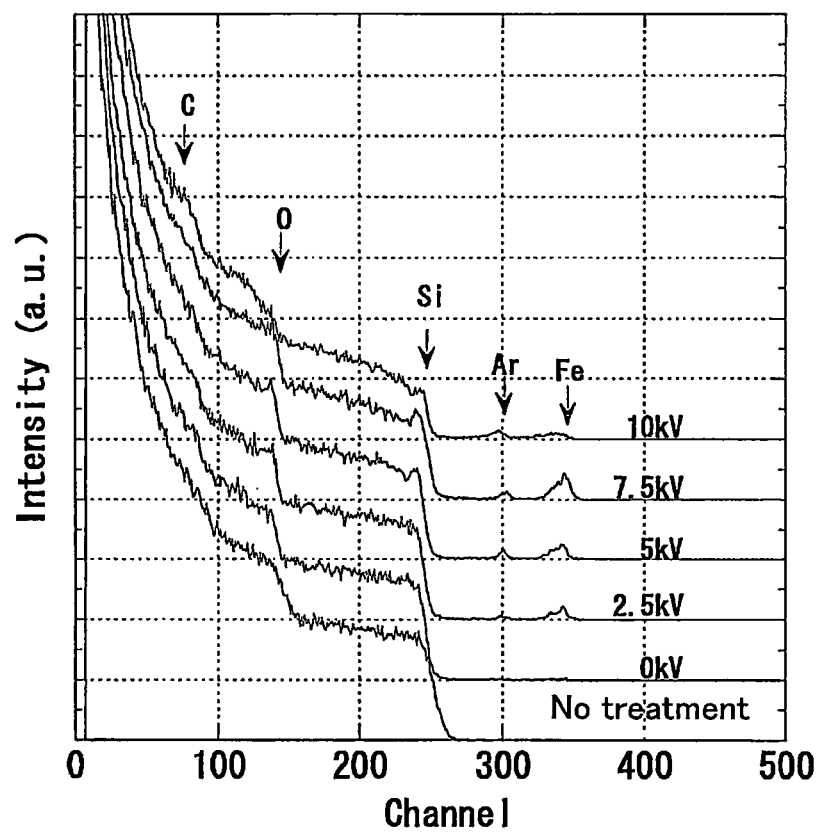
FIG. 9 shows RBS spectra of Ar-plasma-ion-irradiated silicone samples.
Figure 10:
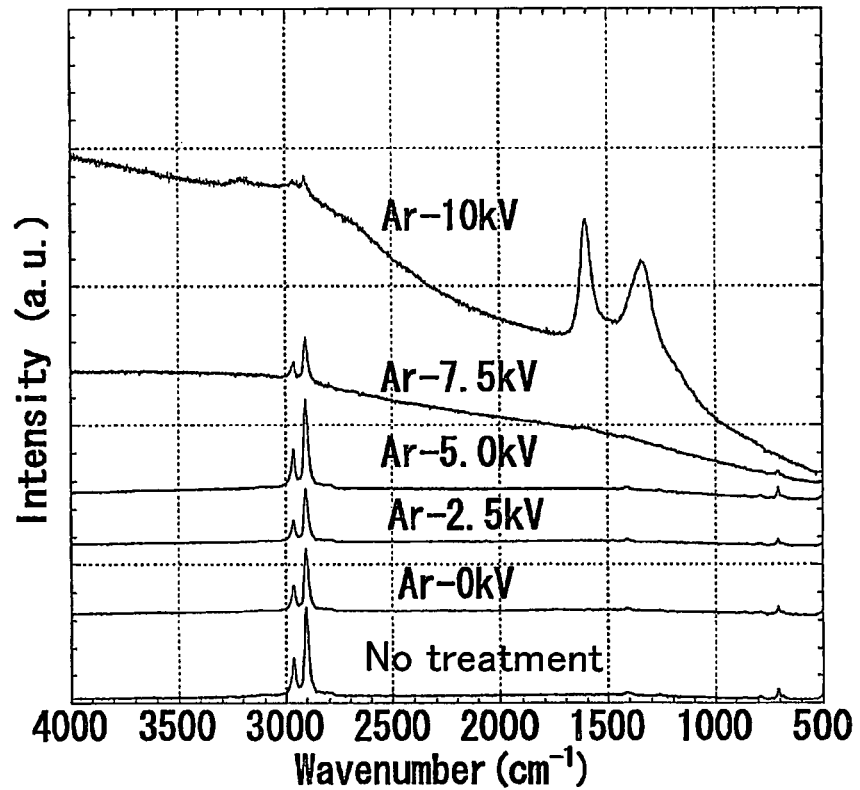
FIG. 10 shows Raman spectra of Ar-plasma-ion-irradiated silicone samples.
Figure 11:
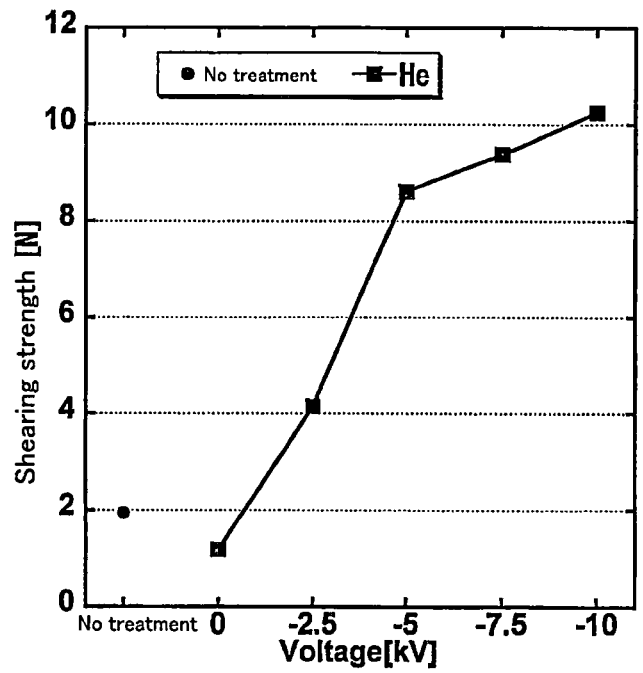
FIG. 11 shows results of adhesion tests for a fibrin adhesive.
Figure 12:
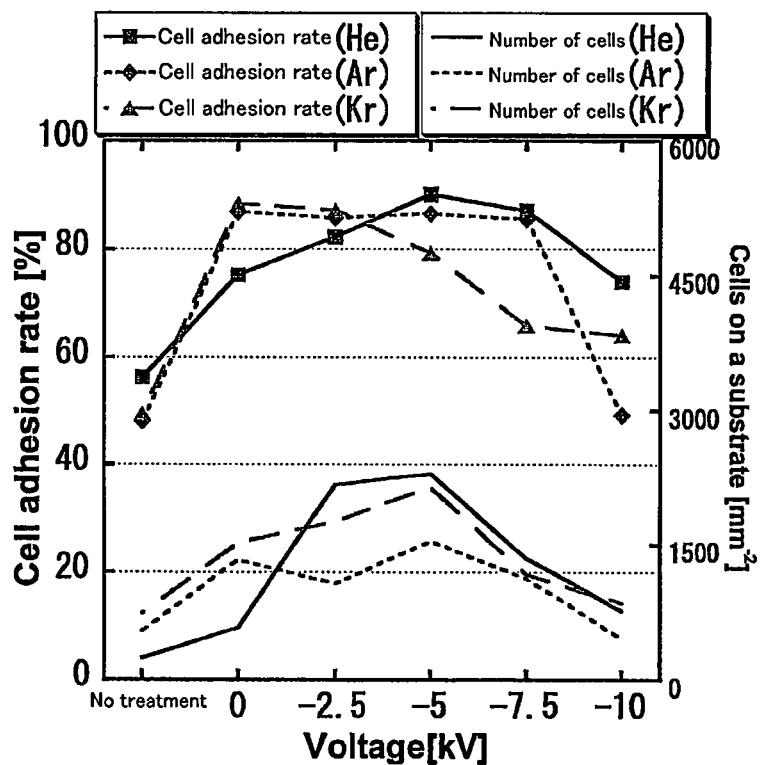
FIG. 12 shows cell adhesion rates and numbers of cells.
Figure 13:
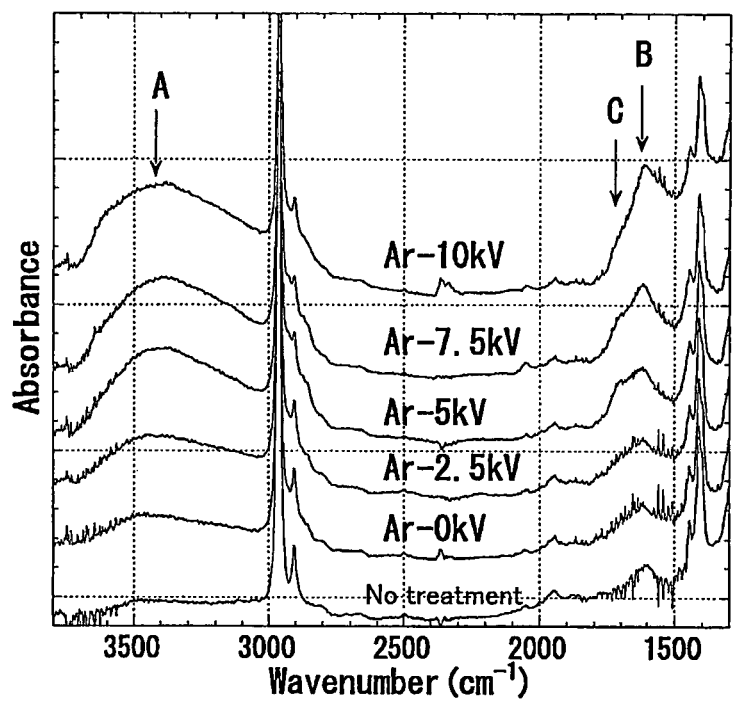
FIG. 13 shows FT-IR spectra of argon-irradiated samples.

The invention claimed is:

1. A medical catheter set that comprises:
  (a) a medical catheter which is composed of material selected from the group consisting of silicone, polyurethane, polypropylene and polytetrafluoroethylene (PTFE), at least a portion of the surface of which is modified by plasma ion implantation;
  wherein the plasma ion pressure during treatment is $1.0 \times 10^{-1}$ to $1.0 \times 10^{-4}$ torr, the treatment time of plasma ion implantation is 1 minute to 3 hours, and a negative voltage of 0 to $-10.0$ kV is applied during plasma ion implantation; and wherein the medical catheter has an improved adhesiveness to fibrin adhesive; and
  (b) a fibrin adhesive, and
  wherein the fibrin adhesive improves fibrin adhesion caused by an increase in carbon proportion at the surface and increase in surface area.

2. The medical catheter set of claim 1 which is composed of silicone.

3. The medical catheter set of claim 1 wherein a high-voltage negative pulse is applied to plasma-exposed material selected from the group consisting of silicone, polyurethane, polypropylene and polytetrafluoroethylene (PTFE) so as to attract ions such that the surface of the material is omnidirectionally irradiated with the ions.

4. The medical catheter set of claim 1 wherein plasma ions are selected from the group consisting of $He^+$, $Ne^+$, $Ar^+$, and $Kr^+$.

5. A method for adhering a medical catheter to a biological tissue which comprises a step of applying, to the biological tissue,
  (a) a medical catheter which is composed of material selected from the group consisting of silicone, polyurethane, polypropylene and polytetrafluoroethylene (PTFE), at least a portion of the surface of which is modified by plasma ion implantation;
  wherein the plasma ion pressure during treatment is $1.0 \times 10^{-1}$ to $1.0 \times 10^{-4}$ torr, and the treatment time of plasma ion implantation is 1 minute to 3 hours, and a negative voltage of 0 to $-10.0$ kV is applied during plasma ion implantation; and wherein the medical catheter has an improved adhesiveness to fibrin adhesive: and
  (b) a fibrin adhesive, and
  wherein the fibrin adhesive improves fibrin adhesion caused by an increase in carbon proportion at the surface and increase in surface area.

6. The method of claim 5 wherein the medical catheter is composed of silicone.

7. The method of claim 5 wherein a high-voltage negative pulse is applied to plasma-exposed material selected from the group consisting of silicone, polyurethane, polypropylene and polytetmfluoroethylene (PTFE) so as to attract ions such that the surface of the material is omnidirectionally irradiated with the ions.

8. The method of claim 5 wherein plasma ions are selected from the group consisting of $He^+$, $Ne^+$, $Ar^+$, and $Kr^+$.

* * * * *